United States Patent [19]

Jacobson et al.

[11] Patent Number: 4,968,672
[45] Date of Patent: Nov. 6, 1990

[54] ADENOSINE RECEPTOR PRODRUGS

[75] Inventors: Kenneth A. Jacobson, Silver Spring; Kenneth L. Kirk, Bethedsa, both of Md.; John W. Daly, Washington, D.C.

[73] Assignee: The United States of America as represented by the Department of Health and Human Services, Washington, D.C.

[21] Appl. No.: 229

[22] Filed: Jan. 2, 1987

[51] Int. Cl.$^5$ .............................................. A61K 31/52
[52] U.S. Cl. ....................................... 514/46; 514/17; 514/18; 514/263; 530/329; 530/331; 530/332; 536/26; 536/27; 544/273
[58] Field of Search .................... 536/26; 514/49, 263, 514/17, 18, 19; 544/273; 530/329-332

[56] References Cited

U.S. PATENT DOCUMENTS 4,696,932 9/1987 Jacobson et al. .

OTHER PUBLICATIONS

Jacobson et al., The Chemical Abstracts, 107: 59455h (1987).

Primary Examiner—Ronald W. Griffin
Assistant Examiner—James O. Wilson
Attorney, Agent, or Firm—Birch, Stewart, Kolasch & Birch

[57] ABSTRACT

A functionalized congener approach to drugs acting at $A_1$ and $A_2$ adenosine receptor types is applicable to prodrug design. The prodrugs affect a more efficient delivery of the drug at the particular site of the body affected and take advantage of selective biochemical cleavages and alteration in distribution characteristics. In particular, kidney functions and lipid functions are stressed in the invention.

13 Claims, 5 Drawing Sheets

Two Modes Of Drug Targeting Using Functionalized Congeners

KIDNEY PRODRUG GENERAL STRUCTURE *

1) acyl group removed by peptidases

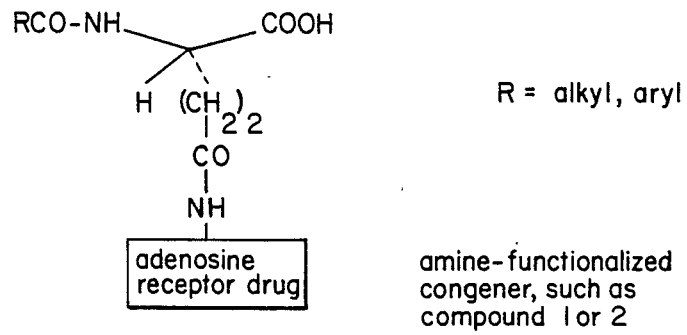

R = alkyl, aryl amine-functionalized congener, such as compound 1 or 2

2) γ-glutamyl bond cleaved specifically in the kidney by - Glu transferase, to release the highly potent amine congener

*This delivery scheme based on γ-Glu transferase has been used previously with certain other drugs which act by mechanisms other than adenosine receptors.

FIG. 4

Synthesis of xanthine derivatives, reagents: a. EtOH/HCl⁻⁻,
50°(53) or R'OH/DMAP/EDAC(54); b. 70% ethylamine, aqueous (55) or ethylene
diamine, neat (56,59); c. DCC/HOBt; d. HBr/HOAc. R=Me, Et, or n-Pr,
corresponding to compound suffixes a, b, and c, respectively.
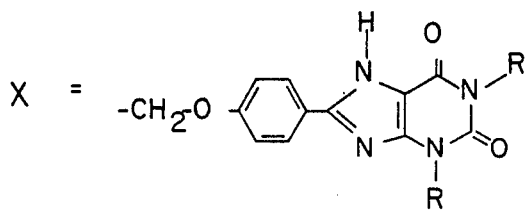
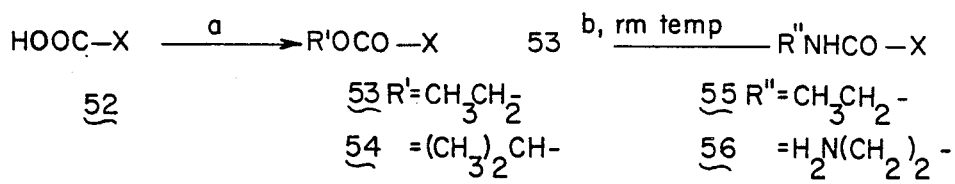
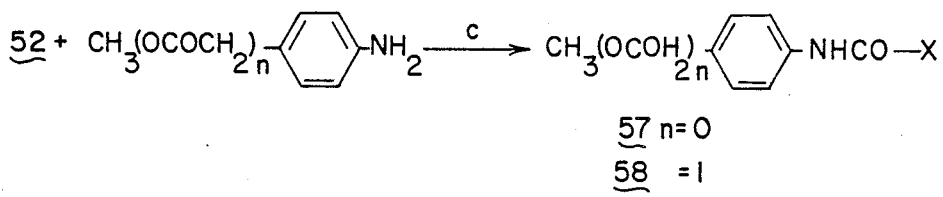
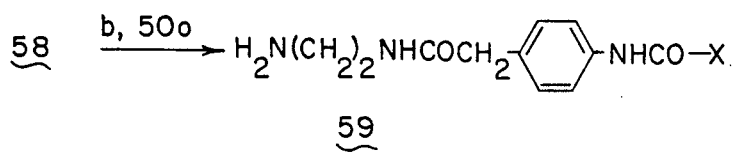
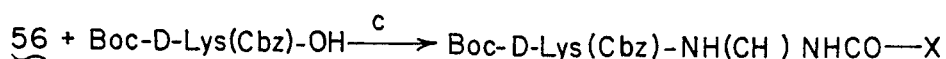
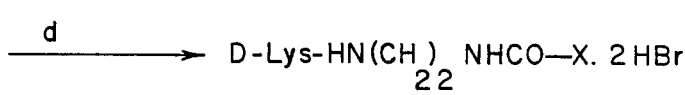
FIG. 5

ADENOSINE RECEPTOR PRODRUGS

BACKGROUND OF THE INVENTION

Adenosine acts as a neuromodulator in the circulatory, endocrine, immune, and central nervous system. The $A_1$-adenosine receptor subtype is generally inhibitory toward adenylate cyclase, and the $A_2$- is stimulatory. Other effector systems in particular ion channels may be regulated by $A_1$ and $A_2$ receptors. Potent and selective analogs of adenosine receptor agonists (adenosines) and antagonists (xanthines) have been developed using the "functionalized congener" approach (J. Med. Chem. 1985, Vol. 28, p. 1334 and p. 1341). Analogs of adenosine receptor ligands bearing functionalized chains were synthesized and attached covalently to various organic moieties, such as amines and peptides. $N^6$-[p-(Carboxymethyl)phenyl]adenosine and 8-p-(carboxymethyloxy)phenyl derivatives of 1,3-dialkylxanthines were synthesized as biologically active functionalized agonists and antagonists, respectively. Attachment of polar groups to the xanthine congeners increased water solubility. Amino congeners derived from the carboxylic acid derivatives of agonists or antagonists had nanomolar $A_1$-receptor binding affinities, as measured by inhibition of binding of tritiated $N^6$-cyclohexyladenosine on rat cerebral cortex membranes. Conjugates of the various functionalized congeners may be useful as high affinity receptor probes in histochemical, chromatographic, or radioligand binding studies.

Adenosine Receptor Prodrugs

Adenosine and some of its more metabolically stable analogs are potentially useful as antihypertensive agents, in part through $A_2$-adenosine receptor-mediated vasodilation. Side effects, including headache, disabling cardiac depression, and sedation, are a limitation to their use.

Caffeine and theophylline are classical examples of methylxanthines which are used clinically as adenosine receptor antagonists. While at clinical doses these drugs act principally through binding at adenosine receptors (of the $A_1$ and $A_2$ subclasses), there are other biochemical actions, such as phosphodiesterase inhibition. Since there are numerous sites of receptor-mediated action of adenosine (and hence xanthines) throughout the body use of these drugs is commonly associated with side effects. Theophylline and caffeine serve as central stimulants, respiratory stimulants, cardiac stimulants, and diuretics, but their use is frequently accompanied by insomnia, palpitations, tremor, and headache. These xanthines freely pass through the blood-brain barrier and therefore cause both central and peripheral effects.

Thus, caffeine and theophylline are non-selective drugs with respect to site and mechanism of action. In addition, they are not particularly potent. Within recent years, adenosine receptor antagonists that are much more potent, and in some cases selective for either the $A_1$ or $A_2$ receptor subtype, have been synthesized. A functionalized congener approach to xanthine analogs has resulted in a series of 1,3-dialkyl-8-phenyl derivatives that bear chains for attachment to carriers. Some of these have high potency, selectivity, bioavailability, and the potential for targeted delivery. Similarly, a functionalized congener approach has been applied to $N^6$-phenyladenosine analogs as adenosine receptor agonists. In general, it has been possible to modulate the pharmacodynamic parameters (strength of binding to the receptor and receptor subtype selectively) of these functionalized congeners as adenosine receptor drugs through distal structural changes. (See FIG. 1.)

It has been shown previously in patent applications that a series of functionalized congeners related to 1,3-dialkyl-8-phenylxanthine act as adenosine receptor anagonists in a manner similar to theophylline, but have considerably greater potency and selectivity. An amine congener, 1a, hereafter referred to as XAC (xanthine amine congener), has been shown to be a selective antagonist at adenosine $A_1$-receptors both in in vitro screening and in cardiovascular models, that involve reversal of the effects of 5'-N-ethylcarboxamidoadenosine (NECA) on blood pressure (hypotensive action associated with $A_2$ receptors) and the heart/negative chronotropic action associated with $A_1$ receptors) in rodents, XAC was found to have a selectivity ratio of approximately 20:1 for $A_1$ receptors in the cardiovascular model. Thus, over a certain range of doses, including 0.1 mg/kg NECA and 0.1 to 1.0 mg/kg XAC, the heart rate remained relatively constant whereas blood pressure diminished to a degree comparable to the absence of XAC, due to the unattenuated vasodilatory ($A_2$) effect of the adenosine agonist. The degree of $A_1$ selectivity may vary considerably depending on which systems and species are being compared.

An adenosine amine congener (ADAC, 1b) was synthesized as an intermediate for conjugates and proved highly potent as an adenosine agonist in vitro and in vivo.

A continuing search for both more potent and more selective adenosine receptor antagonists has resulted in more potent xanthine analogs, such as XAC, and in analogs having selectivity for $A_1$- or $A_2$-adenosine receptor subtypes. However, the development of new adenosine receptor drugs (either agonist or antagonist) has been impeded by the multiplicity of effects mediated by adenosine. Clearly, tissue-specific drug delivery systems for adenosine agonists or antagonists are required to achieve genuine in vivo selectivity. Adenosine receptor-containing organs which are particularly important to target are brain (e.g. antagonists as central stimulants, agonists as anxiololytics and antinociceptive agents), heart (anagonists as cardiotonics, agonists as vasoidilators), lung (antagonists as anti-asthmatics), and kidney (antagonists as diuretics, agonists as antihypertensive agents).

DESCRIPTION OF THE FIGURES

FIG. 4 shows the general structure of the kidney prodrug.

FIG. 5 shows the synthesis of the xanthine derivatives of the present invention.

DETAILED DISCLOSURE

There are here reported new derivatives originating in the functionalized congeners of both agonists and antagonists that as prodrugs are even more selective in their action as adenosine receptor drugs by virtue of selectivity in delivery and/or cleavage at a particular desired site of action. These analogs are more effective at a particular site in the body that contains adenosine receptors than at other sites in the body at which similar adenosine receptors are located. Prodrugs are drug derivatives which are chemically or enzymatically converted to a more potent or effective form (structurally different than the form administered) at a particular site of action. Prodrugs are inherently more specific and associated with fewer side effects than the parent drugs, due to concentration of the drug at the site.

Few prodrug schemes (Bodor et al, J. Pharm. Sci., Vol. 67, pp. 1045-1050, 1978) have been suggested for xanthines such as theophylline, due to the lack of functional groups available for derivatization. We have developed a functionalized congener approach to adenosine receptor agonists and antagonists, by which new functionality is introduced at a distal site on the drug molecule without diminishing receptor binding. In particular, an amine congener of 1,3-dipropyl-8-phenylxanthine, XAC, compound 1a, was more potent than the parent drug, and this enhancement of receptor binding affinity was dependent on the presence of a free amino group. We show here that the amino group of XAC may be blocked temporarily, in a way which diminishes activity but which is reversible at a site of action, e.g., the kidneys. The structural flexibility offered by the functionalized congener approach thus permits the application of prodrug delivery schemes otherwise inaccessible for a particular class of drugs.

Figure 1:
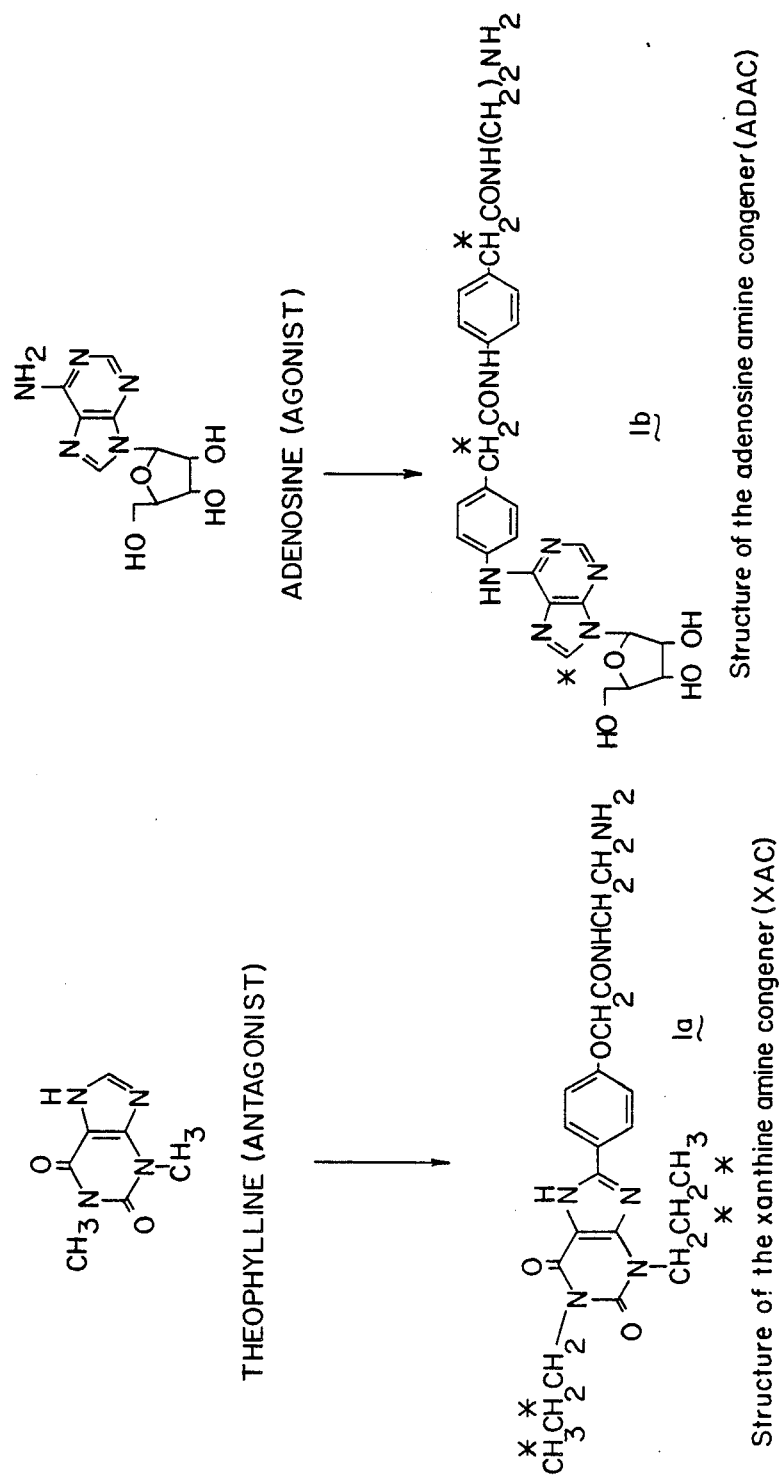
FIG. 1 illustrates the structure of XAC and ADAC.
Figure 2:
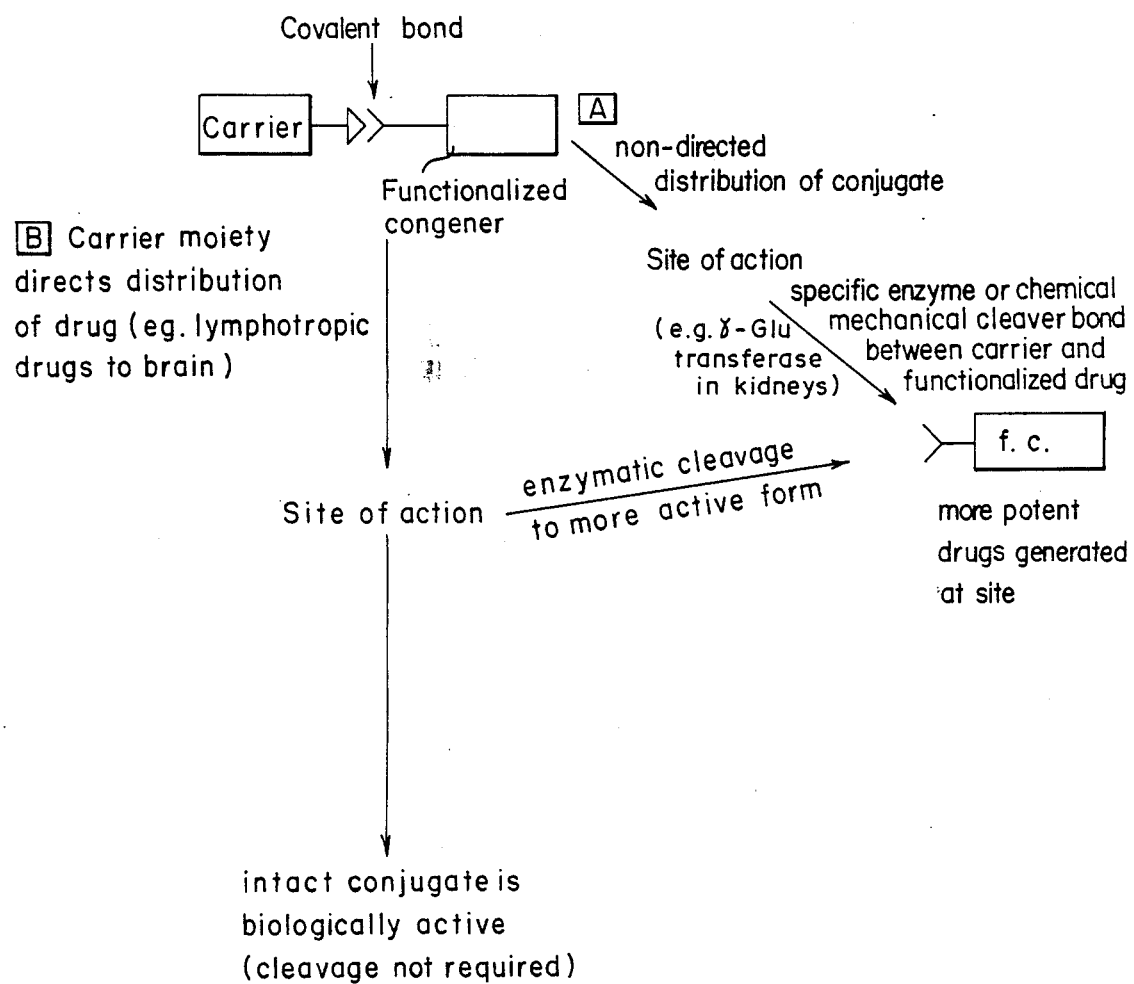
FIG. 2 illustrates two modes of drug targeting using functionalized congeners.

Two modes of drug targeting using functionalized congeners are outlined in FIG. 2. The symbol (—<) stands for newly created functionalized chain covalently attached to the drug. Route A is a standard prodrug approach, in which a less active form of the drug is administered leading to specific biochemical activation and concentration of the more active species at a particular site in the body. The chemical reactions leading to activation are typically an enzymatic hydrolysis or an oxidation reaction. The functionalized congener may be linked to the temporary blocking group via an ester, amide, thioester, thioamide, urethane, imide, silylamine, acyloxymethylamino, acylaminomethylamino, imine, oxymethylamino, or other oxyakylamino linkage. Examples of prodrugs acting through Route A are in Table 1.

Route B represents the case in which the intact conjugate (functionalized drug covalently coupled to "carrier") is sufficiently potent to produce the desired biological effect. Although not strictly "prodrugs", some of the derivatives synthesized (e.g. 37) was highly potent in the blocked form and required no cleavage step is required. The advantage of Route B over the parent drug is that the carrier alters the distribution of the drug in the body. For example, if a lipid group is contained in the carrier, the drug is less polar and may be absorbed more readily from the gut, when administered orally.

Table 2 lists prodrugs (including Routes A and B of FIG. 2) and chemical intermediates, based on xanthine and adenosine functionalized congener and the method of synthesis. The potency of each compound at $A_1$ adenosine receptors is indicated by the $K_i$ (inverse relationship to potency) in a membrane binding assay.

Applications of Functionalized Congeners of Adenosine and Xanthines to the Kidney Theophylline has been known to act as a diuretic, although this is not its major clinical use at the present time. It has been shown that theophylline causes increased natriuresis and spares potassium. This diuretic effect occurs through the mediation of cell surface adenosine receptors, at which xanthines such as theophylline act as competitive antagonists to endogeneous adenosine.

The $A_1$-adenosine receptor has been found to govern the vasoconstriction response of the efferent (preglomerular) renal arteriole. Adenosine and other adenosine agonists cause a reduction in the blood flow to the kidney and thus a reduction in the glomerular filtration rate. This is the only site in the body at which adenosine causes a vasoconstriction. The $A_2$-adenosine receptor also causes a reduction in the glomerular filtration rate is due to dilation of the efferent (pre-glomerular) renalarteriole. Adenosine and other adenosine agonists cause a reduction in the blood flow to the kidney and thus a reduction in the reduction in the glomerular filtration rate due to dilation of the efferent (postglomerular) renal arteriole. Thus, blocking the effects of adenosine at either receptor subtype by xanthines produces a rise in the glomerular filtration rate and thus an increase in the rate of urine formation. Tubular effects as well as hemodynamic effects may contribute to the diuretic action of the xanthines.

Figure 3:
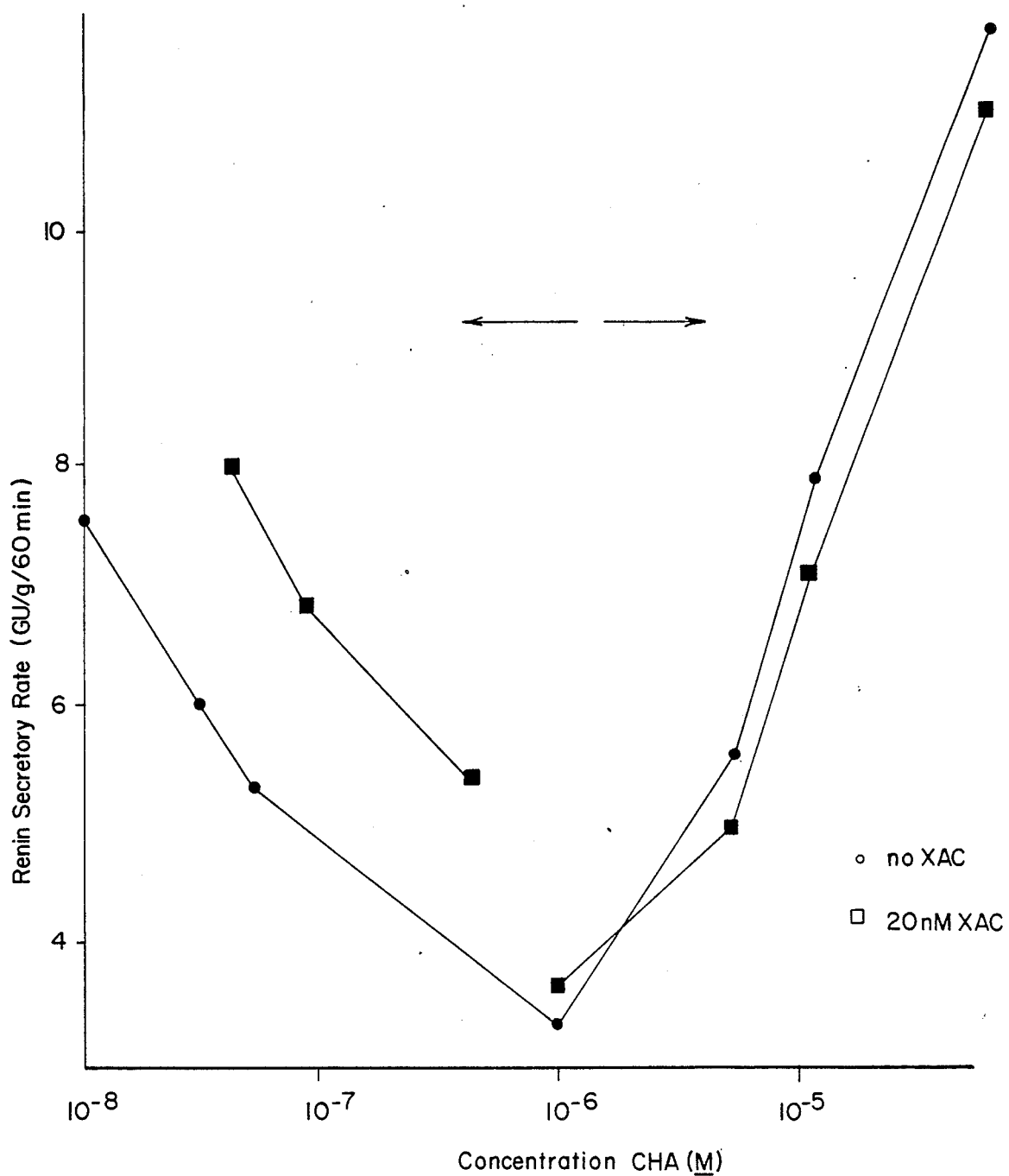
FIG. 3 shows the effect of XAC on kidneys.

XAC, 1a, similar to theophylline, acts as an adenosine antagonist in the kidneys, except that it is orders of magnitude more potent than theophylline and is $A_1$ selective. (FIG. 3) An $A_1$ selective adenosine antagonist may be preferable as a diuretic since it does not decrease the total blood flow to the kidney. However some combination of $A_1$ and $A_2$ antagonism may be desirable. By selecting the appropriate amine congener to be administered directly or to be incorporated into a prodrug from a family of xanthine amine congeners (see below) having a range of $A_1/A_2$ selectivity ratios one may vary the in vivo selectivity.

Delivery of Adenosine Receptor Drugs to the Kidney

The xanthine and adenosine functionalized congeners are ideally suited for the prodrug approach due to the presence of chemical functional groups at sites which are relatively insensitive to steric bulk in the receptor-bound state. It has been shown that XAC, 1a, and ADAC, 1b, are suitable functionalized congeners which can be attached to certain carriers with the retention of biological activity. It was noted that in both the agonist and antagonist series, the presence of an amino group on the attached chain greatly enhanced the potency of binding to the receptor. Blocking the amino group by an uncharged moiety generally diminished the by at least an order of magnitude and this parallels a drop in in vivo potency. The presence of a carboxylic acid group on the chain is associated with relatively low potency at adenosine receptors. Therefore, acylation of the amine functionality was chosen as an approach to the development of prodrugs (amine as site of temporary blocking), since it seemed that a neutral or anionic derivative would possibly be less potent as an adenosine receptor antagonist.

A drug delivery approach for the kidney utilizing gamma-glutamyl derivatives of amine-bearing drugs was introduced by Orlowski, et al (J. Pharm. Exp. Ther. 212:167-172, 1979). They bound a precursor, dopa, of the neurotransmitter, dopamine, and the antibiotic, sulfamethoxazole, at the gamma carboxylic position of glutamic acid derivatives and noted an accumulation of the neurotransmitter and antibiotic in the kidneys. This accumulation was assumed to occur through the substitution of the gamma-glutamyl bond by another amine (thus releasing the drug) by the action of gamma-glutamyl transferase, known to be present in high concentration in the kidneys in comparison to other organs, such as heart, lungs, and intestines. In a further study of drug latentation by gamma-glutamyl transpeptidase (Magnon, et al, J. Med. Chem. 25:1013-1021,1982), it was found that some amine-bearing drug derivatives are amenable to this prodrug cleavage scheme, while others are not readily cleaved by the enzyme.

Gamma-glutamyl derivatives (general formula in FIG. 4) of adenosine receptor amine congeners were synthesized by the routes shown below:

on the cleavage of the gamma glutamyl bond to liberate XAC at the site of action.

As shown in the table four, the prodrug, 17, has a selective effect in kidney function compared to effects on other organs at the same dose. The hypotensive effect of adenosine agonists (action on the non-renal vasculature) is reversed by XAC, but not by the prodrug, 17.

There are several secondary advantages of compound 17 as a prodrug. Due to the presence of the free Scheme 1

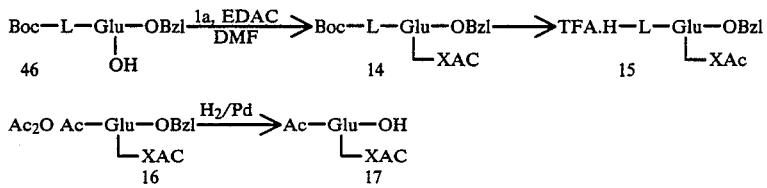

Scheme 2a

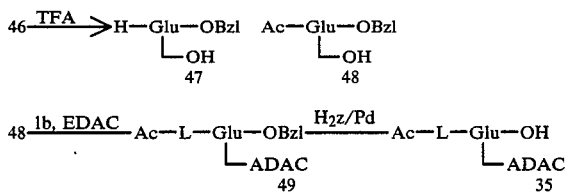

Scheme 2b

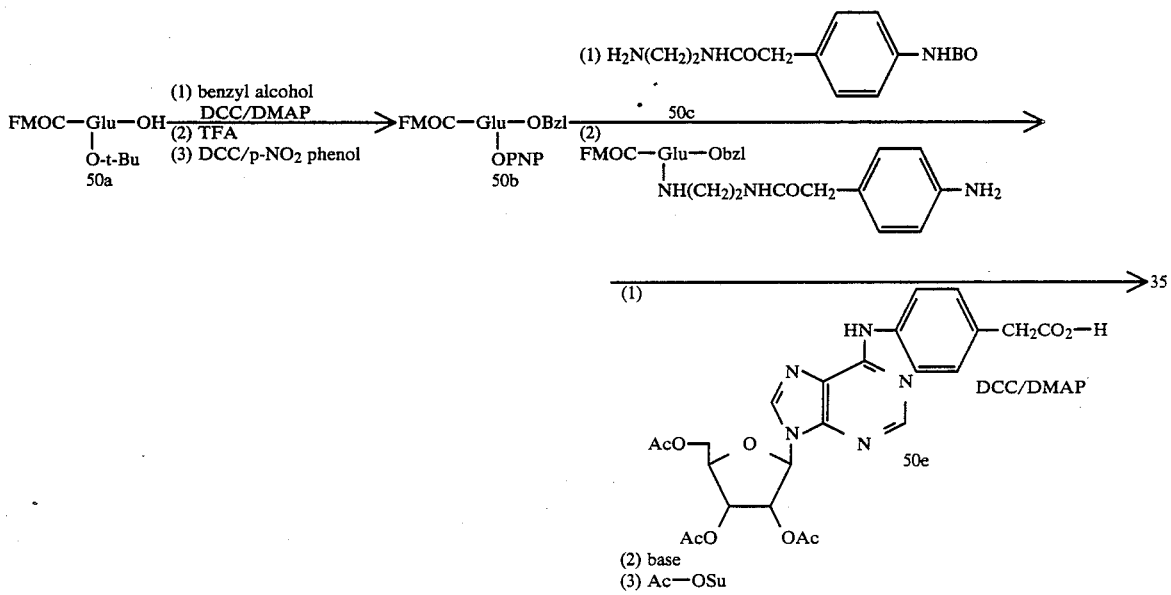

Compound 17 acted as a prodrug delivery system for XAC in vivo. $N^6$-Cyclohexyladenosine was administered to rats to lower the glomerular filtration rate to a level 30-40% of normal. XAC, administered I.V. at a dose range of 5-50 ug/kg (at least a thousand fold less than the dose of theophylline required to produce a comparable change) produced a dose dependent reversal of the effects of the adenosine agonist (Table 3). Thus XAC acts as a diuretic in the adenosine depressed kidney. The prodrug, compound 17, produced an even greater return of glomerular filtration rate than did XAC. Since the receptor binding potency of XAC is 200-fold greater than that of prodrug 17, the effect is not due to the intact prodrug, but must rather be dependent carboxylate group, entry into the brain is impeded. Thus, side effects of the xanthine acting as a central stimulant are not observed.

Furthermore, compound 16 constitutes an orally active form of the drug, since it is sufficiently non-polar to be absorbed effectively by the gut. Once in circulation the benzyl ester is readily cleaved by estereases to liberate compound 17, which may then act as a prodrug. Thus a cascade effect of prodrugs is achievable, with XAC finally being liberated in the kidneys. Compound 16 is readily dissolved in ethanol, with warming. Thus an ethanolic solution is a suitable vehicle for the oral administration of the drug.

Compound 35 is a prodrug of the potent and $A_1$-selective adenosine agonist ADAC, 1b. This conjugate causes ADAC to be delivered to the kidney by the same mechanism as above. Like other adenosine agonists, ADAC causes a decrease in renin release by the kidney which in turn results in a lowering of blood pressure. Thus, compound 35 has potential for development as an antihypertensive agent based on the adenosine receptor system. The central side effects seen with other adenosine agonists such as CHA and NECA are absent, because compound 35, as well as ADAC, are excluded from passage across the blood brain barrier.

Diuresis is not the only use of kidney-directed xanthines. Perhaps a more medically significant application is in the reversal or prevention of acute renal failure. Adenosine as an endogenous mediator of hemodynamic changes is thought to have a role in the mechanism of acute renal failure. Adenosine is released in the "energy deficient state" thought to accompany ischemic and nephrotoxic models of acute renal failure. The protective effect of xanthines as adenosine antagonists against kidney failure has been studied (Bidani and Churchill Can. J. Physiol. and Pharmacol., 61:567–571, 1983. and Bowmer et al., Brit. J. Pharmacol 88:205–212, 1986).

Models for studying kidney failure include injuries resulting from ischemia from occlusion of one renal artery or from glycerol injection. Theophylline and the synthetic xanthine analog, 8-phenyltheophylline have beneficial effects in preventing or lessening the severity of resultant kidney failure, and in increasing survival.

XAC or the prodrug derivative, compound 17, act in the same manner except for considerably greater potency and selectivity. Central side effects are not observed, and cardiac and other side effects are not a factor due to the tissue targeting of the prodrug. Thus, this group of compounds may have tremendous clinical utility in reducing the severity of acute kidney failure.

Lipids

A discussion of and definition of lipids is found in Lehninger, *Principles of Biochemistry*, 1982, Worth Publishers, Inc., page 303.

The most abundant kinds of lipids are the fats or triacylglycerols, which are major fuels for most organisms. Indeed, they are the most important storage form of chemical energy. Polar lipids (including phospholipids, another class) are major components of cell membranes, the "containers" in which metabolic reactions occur.

Lipids of this invention are depicted in claims 7 through 10.

Lymphotropic Drugs Based on Adenosine Receptor Functionalized Congeners

Certain drugs have been attached covalently to lipids to afford a carrier system for entry of the drug into the lymphatic system. The advantages of this mode of entry from the intestines is that (1) the drug is targeted to particular organs such as the brain and (2) metabolism by the liver, which normally occurs when the drug circulates in the blood stream, is delayed.

1,3-Dipalmitoyl derivatives of L-dopa (Garzon-Aburbeh et al. J. Med. Chem., 29:687, 1986) were used to deliver the drug to the brain and effect a treatment of Parkinson's disease superior to the use of L-dopa alone. A similar strategy was used for derivatives of the neurotransmitter gamma-aminobutyric acid (Jacob, et al. J. Med. Chem. 28:106–110, 1985).

By the functionalized congener approach it is possible to synthesize a lipid derivative that remains active at the receptor binding site, thus there is no need for a cleavage step (Route B, FIG. 2). Certain lipid conjugates are active at the target organ immediately. Below is a list of representative lipid derivatives of adenosine antagonists (potencies at A1 adenosine receptors in Table 2).

Whereas the xanthine carboxylic congener, XCC, 30, or the amine congener, XAC, 1a, do not enter the brain appreciably due to the presence of charged groups. At a dose of 1 mg/kg I.V. in rats the xanthines are undetectable in the brain, i.e., less than 1/20 the conc. in plasma (plasma conc. after 10 min=2.65±0.45 ug/ml). The above lipid derivatives will enter the brain and should be able to act as central stimulants. When given orally, the lipid derivatives enter the lymphatic system and may be directed to the brain. Compound 43 (as its reduced dihydropyridine form) is designed to enter the brain by another mechanism.

When the myristoyl amide, compound 33, is hydrolyzed, a product (XAC, 1a, Ki=1.2 nM) having two orders of magnitude greater potency at adenosine A1 receptors is formed. Compound 33 is readily cleaved at the site of action to generate XAC, a more potent antagonist, thus it is a true prodrug (Route A, FIG. 2). Compound 32 is a lymphotropic drug which does not require cleavage to be active, since the conjugate and one of its hydrolysis products, XCC, 15, are of comparable potency.

Chemical Structures—Lymphotropic Druqs

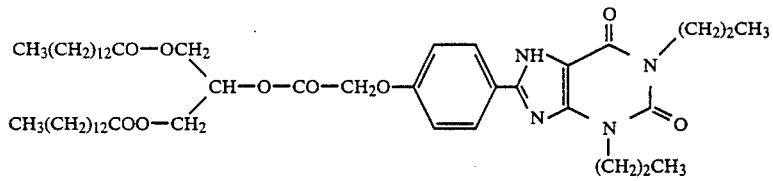

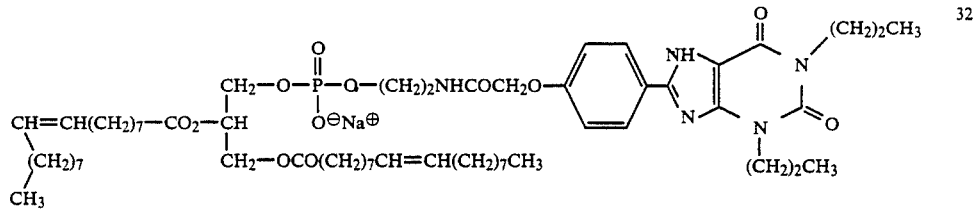

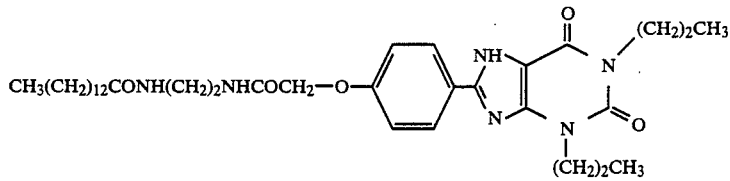

33

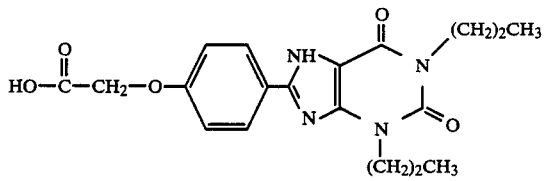

15

New Functionalized Congeners of Adenosine Receptor Drugs

The synthesis of potent and/or selective analogs of caffeine and theophylline as antagonists at extracellular adenosine receptors remains a challenge. Two adenosine receptor subtypes have been delineated on the basis of inhibition ($A_1$) or stimulation ($A_2$) of adenylate cyclase by adenosine and adenosine analogues. Numerous physiological functions have been shown to be regulated by either or both $A_1$ and $A_2$ adenosine receptors. In many organs and cell lines, a single receptor subtype has been found to occur. For example, in platelets and PC12 pheochromocytoma cells the existing adenosine receptors appear to be all of the $A_2$ subtype. Fat cells are considered to contain only the $A_1$-receptor subtype.

In addition to the functionalized congeners specified in our previous patent applications (for xanthine derivatives as antagonists: U.S. application Ser. No. 717,616 and for $N^6$-substituted adenosine derivatives as agonists: U.S. application Ser. No. 717,624), we have developed additional series of functionalized congeners, which are of different potency and receptor subtype selectivity. Chemical derivatives of these congeners may be delivered selectively by the prodrug schemes described in previous sections.

The new functionalized congeners in the xanthine series include new amine congeners (e.g. 12,19), hydroxy congeners (e.g. 39), and carboxylic congeners (e.g. 6,44,45). The hydroxy congener, 39, may be derivativatized as esters (as in the lipid derivatives 41 and 42) as prodrugs. The carboxylic congener, 44, contains an FMOC (9-fluorenemethyloxycarbonyl) protecting group which may be removed after coupling of the carboxylate, to enhance potency at adenosine receptors through the presence of an amino functionality.

Additional amide derivatives of a carboxylic acid congener of 1,3-dialkylxanthine, having a 4-[(carboxymethyl)oxy]phenyl substituent at the 8-position, have been synthesized (FIG. 5 and Table 5) in order to identify potent antagonists at $A_2$-adenosine receptors stimulatory to adenylate cyclase in platelets. Distal structural features of amide-linked chains and the size of the 1,3-dialkyl groups have been varied. 1,3-Diethyl groups, more than 1,3-dimethyl or 1,3-dipropyl groups, favor $A_2$-potency (Table 6), even in the presence of extended chains attached at the 8-(p-phenyl) position. Polar groups, such as amines, on the chain simultaneously enhance water solubility and $A_2$-potency. Among the most potent $A_2$-ligands are an amine congener, 8-[4-[[[[(2-aminoethyl)amino]carbonyl]methyl]oxy]-phenyl]-1,3-diethylxanthine, and its D-lysyl conjugate, which have $K_B$-values of 21 and 23 nM, respectively, for the antagonism of 5'-N-ethylcarboxamidoadenosine-stimulated adenylate cyclase activity in human platelet membranes. Strategies for the selection and tritiation of new radioligands for use in competitive binding assays at $A_2$-adenosine receptors have been considered.

Characterization of adenosine receptors with reversibly-binding radioligands has been carried out mainly with brain membranes, due to the high density of $A_1$ receptors in that organ. A number of radioligands for $A_1$ receptors have been reported. Tritiated $N^6$-cycloalkyladenosines and tritiated R-$N^6$-phenylisopropyladenosine having high specific activity are used regularly in competitive binding assays to determine affinity of new analogs at $A_1$-receptors. The choice of antagonist radioligands had been limited to [$^3$H]1,3-diethyl-8-phenylxanthine ([$^3$H]DPX), 1b, which has a $K_i$ at $A_1$-receptors of about 60 nM. [$^3$H]XAC, 1b, a 1,3-dipropylxanthine amine congener, has a higher affinity and specific activity than [$^3$H]DPX, and its use overcomes a number of difficulties associated with the use of [$^3$H]DPX as an antagonist radioligand for $A_1$-receptors.

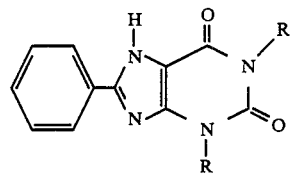

51a R = Me
51b    = Et
51c    = Pr

Although a number of moderately $A_2$-selective antagonists have been reported, none are of sufficiently high affinity to serve as radiotracer for competitive binding studies. For this reason, we approached the development of an $A_2$-antagonist radioligand from the standpoint of maximizing $A_2$-potency regardless of the selectivity ratio. At that point a highly potent candidate should be radiolabeled and its binding properties examined in a membrane preparation such as human platelets in which $A_2$- but not $A_1$-adenosine receptors are present. Subsequently, the platelet assay is to be used to study other potential $A_2$-adenosine ligands by measuring their inhibition of binding of a well-characterized radioligand.

The classical approach to developing new drugs has been to explore the effect of structural modifications at or around a primary pharmacophore. We have developed a "functionalized congener approach" for adenosine receptor ligands, by which a chemically functionalized chain is incorporated at a point that does not reduce biological activity. The resulting active congener can be joined covalently to a variety of moieties, including amino acids and peptides or solid supports for affinity chromatography, through a functional group such as an amine or a carboxylic acid. For xanthines as adenosine antagonists it has been shown that distal structural changes on a chain attached through the 8-(p-phenyl) position can modulate the potency and selectivity of the drugs, perhaps through interactions at sites on the receptor distal to the binding site for the pharmacophore. We now show the validity of this approach for xanthines as antagonists at $A_2$-adenosine receptors.

The $K_i$-values for reversal of 2-chloroadenosine-stimulated cyclic AMP production in guinea pig brain slices for a carboxylic acid congener, 52c, an ethyl ester, 53c, and an amine congener, 1a (all R=Pr) and a p-toluide, 57a (R=Me) were 34, 30, 49, and 20 nM, respectively. Furthermore, within a series of amino acid conjugates of 1a, the D-lysyl conjugate, 1c, displayed high potency, high water solubility, and stability to enzymatic hydrolysis. As modifications of these xanthines designed to increases $A_2$-potency we have explored changing the size of the 1,3-dialkyl groups and incorporating distal amino groups in the functionalized 8-phenyl moiety.

As reported previously, the affinity of XAC, 1a, for $A_2$ receptors of human platelets was in close agreement with the value in brain slices, but the potency of 2c showed a discrepancy between these two systems.

In each case the potency of the 1,3-diethyl analogue at platelet $A_2$-receptors was greater than the 1,3-dimethyl analogue and at least as great as that of the 1,3-dipropyl analogue. The enhancement of $A_2$ affinity by ethyl substituents was more marked for the simple 8-phenyl series, 51, than for the functionalized congeners. In contrast, 1,3-dipropyl-8-phenylxanthine is about 5-fold more potent than the diethyl analog in inhibition of [$^3$H]NECA binding to a striatal $A_2$-adenosine receptor.

While the carboxylic acid congener, 52c, was not particularly potent, esterification to give compound 53c increased potency markedly at $A_2$ receptors, but not at $A_1$ receptors. A comparison of ethyl and isopropyl esters showed preference of the branched isopropyl group at $A_2$ receptors.

Compounds 57a and 57b, containing the p-toluide group, were not as potent at $A_2$-receptors as expected based on previous studies. However, when the 2-aminoethylaminocarbonyl group was attached to the p-methyl group of the toluide, as in 9, the potency rose. Thus, the potency-enhancing effect of a distal amino group, observed consistently with the $A_1$-receptor particularly with dipropyl analogues (e.g., 1a, 61c), now appears to apply as well to the $A_2$-receptor. The enhancement of $A_2$ potency by an amino group is also evident in comparing the ethyl amide, 5, and the 2-aminoethyl amide, 56b.

The potencies of XAC, 1a, and the diethyl analogue, 56b, were nearly identical at $A_2$ receptors but differed by an order of magnitude at $A_1$-receptors. Thus 56b is nonselective for receptor subtypes. Certain alkyl substitutions of the NH's (ethylene diamine moiety) of XAC increase $A_1$-potency. Thus, the tri-methyl substition of 56b produces an antagonist with a Ki of 1.5 nM. Other structural features, such as a 2-hydroxyl group present on the 8-phenyl ring result in greater $A_1$-selectivity. For example, the 2-hydroxyl analog of XAC, 1b, has a Ki at central $A_1$-receptors of 2.3 nM and a Kb for the reversal of NECA-stimulated adenylate cyclase activity in human platelets of 140 nM.

The polarities of the amine congeners varied considerably affecting distribution characteristics such as exclusion from the CNS (more polar favored) and absorption from the intestines (less polar favored). The octanol/water partition coefficients (log p) are as follows: 0.63(56a), −0.06 (56b), 0.81 (1a), −0.05 (59a), and −1.20 (61b). Thus, there is a large difference in polarity between 1,3-diethyl (e.g., 56b) and 1,3-dipropyl (e.g., 1a) analogues, which is also reflected in maximum aqueous solubility (pH 7.2,0.01 M phosphate) of 500 uM and 90 uM, respectively. In 0.1 M acetic acid compound 1a has a maximum solubility of 5 mM. The lipophilic contribution of an additional ring and amide bond in the chain, as in 59a, is roughly equivalent to substituting 1,3-dimethyl with 1,3-diethyl substituents.

EXAMPLES

Example 1

Adenosine and its analogs selective for the $A_1$ subclass of receptors, such as $N^6$-cyclohexyladenosine (CHA), produce renal vasoconstriction in vivo and in vitro. To measure effects of the adenosine receptor antagonists XAC and theophylline, studies were performed in isolated rat kidneys perfused at constant flow with a nonrecirculated medium (Krebs-Hensleit saline supplemented with 3.5 g % Ficoll, 1 g % albumin, 180 mg % glucose and 89 mg % beta-alanine). After a 45 minute period of equilibration at a pressure of 100 mm Hg, flow was maintained at the rate obtained during the final 15 minutes of equilibration and pressure was allowed to vary. Changes in pressure were measured as the difference in pressure from baseline in response to CHA, in the presence or absence of antagonist. $10^{-8}$ and $3 \times 10^{-8}$ M CHA resulted in pressure changes of $5 \pm 2$ and $21 \pm 5$ mm Hg, respectively. Theophylline at $5 \times 10^{-5}$ M produced a shift in the dose-response relationship such that three times the concentration of CHA was required to produce the same response; XAC at $2 \times 10^{-8}$ M produced a similar shift. The calculated inhibitory constants, $K_i$, for theophylline and XAC were $2.6 \times 10^{-5}$ and $1 \times 10^{-8}$, respectively. Thus, XAC is three orders of magnitude more potent than theophylline in blocking CHA-induced renal vasoconstriction.

Example 2

Synthesis: In connection with Scheme 2b

FMOC-L-glutamic acid gamma-t-butyl ester (50a, Sigma, 0.45 g) was esterified in the alpha position using the carbodiimide/4-dimethylaminopyridine method. The t-butyl ester was removed by treatment with neat trifluoroacetic acid for one hour. The gamma carboxylate group was then converted in situ (in ethyl acetate) to the p-nitrophenyl ester, using DCC and p-nitrophenol. The mixture was filtered, washed (acid/base), and evaporated leaving a solid residue. The product, 50b, was recrystallized (ethyl acetate/hexanes) to give an overall yield of 57% (0.35 g), mp. 103°–105° C.

4-Aminophenylacetic acid methyl ester was then acylated using di-t-butyloxycarbonyl dicarbonate (in methanol/water, 1:3; 4 eq. sodium bicarbonate) to a give an amorphous, white solid. This solid was treated with neat ethylenediamine and heated at 50° C. for 15 min. Repeated evaporation and ether addition resulted in a small amount of white precipitate. Water was added and the mass of waxy, amorphous solid, N-t-butyloxycarbonyl-4-(aminoethylaminocarbonylmethyl)aniline (compound 50c), was collected. Compound 50c and FMOC-L-glutamyl-alpha-benzyl-gamma-p-nitrophenyl ester, 50b, were combined in ethyl acetate and the product amide (an oil) was deprotected with trifluoracetic acid to yield compound 50d as a clear oil. The NMR and mass spectra were consistent with the assigned structure.

The protected intermediate carboxylic acid 50e was synthesized by treating N6-(p-carboxymethylphenyl)adenosine with an equivolume mixture of acetic anhydride and pyridine (4 hours). After repeated evaporations with toluene, the product was isolated (36% yield) as a white solid (mp. 125°-130° C. dec) by ethyl acetate extraction from an aqueous solution followed by recrystallization from ethyl acetate/ether.

Compounds 50d and 50e were condensed using the DCC/DMAP method to give FMOC-glutamyl-gamma-(2',3',5'-triacetyl)ADAC-alpha-benzyl ester ,49. Treatment with base followed by acetylation of the alpha amino group with N-hydroxysuccinimidyl acetate gave compound 35.

Example 3

Xanthine analogs were synthesized as previously reported or by routes shown in the Figure. HPLC grade dimethylformamide (Aldrich Chemical Co., Milwaukee, Wis.) was used without further purification. New compounds were characterized by 300 MHz proton NMR using a Varian 300XL and gave spectra consistent with their structures. Except for compounds 10 and 11, chemical ionization mass spectra (CIMS) using ammonia gas were obtained with a Finnigan 1015D spectrometer with a Model 6000 data collection system. Samples for elemental analysis and biological testing were shown to be homogenous by thin layer chromatography (silica, CHCl$_3$/MeOH/HOAc,85:10:5 and 10:10:1), and, if necessary, recrystallized from solvent mixtures including DMF/ether, DMF/water, or DMSO/ether.

Partition coefficients were determined by addition of a dimethylsulfoxide solution (5 uL) of the xanthine to an equivolume mixture (2 mL) of n-octanol and aqueous sodium phosphate, pH 7.2, 0.1 M. After thorough mixing of phases and separation, the ratio of concentrations was determined by comparing absorption at 310 nm of aliquots diluted in methanol (the aqueous phase was filtered). The ±s.e.m. for six determinations corresponded to 0.01 log p units.

Measurements of the potencies of the xanthines as antagonists of NECA-induced stimulation of adenylate cyclase activity in human platelet membranes and as inhibitors of [$^3$H]PIA binding to rat cerebral cortex membranes were carried out as reported previously. The slopes of the inhibition curves had Hill coefficients of about 1.0 and all compounds completely inhibited the response to NECA or the specific binding of [$^3$H]PIA.

8-[4-[(Carboxymethyl)oxy]phenyl]-1,3-diethylxanthine 2-Propyl Ester (54b).

Compound 52b (20 mg, 56 umol) was suspended in a solution of 4-(dimethylamino)pyridine (7 mg) and 2-propanol (0.1 mL) in dimethylformamide (1 mL) and treated with 1-ethyl-3-(3-dimethylaminopropyl)-carbodiimide.HCl (24 mg, 110 umol). After two hours, water (3 mL) was added, and the white solid was collected, washed with water, and dried giving 15.8 mg of compound 54. CIMS (NH$_3$), m/e 401 (M+1)$^+$.

8-[4-[[[(2-Aminoethyl)amino]carbonyl]methyl]oxy]-phenyl]-1,3-diethylxanthine (56b)

Compound 53b (70 mg, 0.18 mmol) was dissolved in ethylenediamine (2 mL) with stirring. The solvent was evaporated under a stream of nitrogen. The oily residue was triturated with methanol and ether to give compound 56b (67 mg, 92% yield) as a solid. CIMS (NH$_3$), m/e 401 (M+1)$^+$.

Alternatively, the carboxylic acid, 52b, was preactivated with 1-ethyl-3-(3-dimethylaminopropyl)carbodiimide.HCl and 1-hydroxybenzotriazole hydrate in dimethylformamide and this mixture was added slowly to a solution of one equivalent of ethylene diamine. The product, 56b, was isolated by thin layer chromatography (CHCl$_3$:MeOH:HOAc, 10:10:1, on silica gel plates) in 44% yield (determined by UV).

8-[4-[[[(4-Carboxymethyl)anilino]carbonyl]methyl]oxy]-phenyl]-1,3-diethylxanthine Methyl Ester (58b).

Compound 52b (80.8 mg, 0.23 mmol), methyl (p-aminophenyl)acetate hydrochloride (55 mg, 0.27 mmol), HOBt (31 mg, 0.23 mmol), and finally 1-ethyl-3-(3-dimethylamino-propyl)carbodiimide.HCl (98 mg, 0.46 mmol) were combined with stirring in 8 mL dimethylformamide. Diisopropylethylamine (39 uL, 0.23 mmol) was added, and the mixture was stirred overnight. Water was added, and the product (60 mg) was collected, washed with water, and dried. CIMS (NH$_3$), m/e 506 (M+1)$^+$.

8-[4-[(Carboxymethyl)oxy]phenyl]-1,3-diethylxanthine 2-(D-Lysylamino)ethylamide Dihydrochloride (61b).

Compound 6b (50 mg, 0.13 mmol) was suspended in 2 mL of dimethylformamide and treated with N -Boc-N -Cbz-D-lysine (95 mg, 0.25 mmol), HOBt (17 mg, 0.13 mmol), and 1-ethyl-3-(3-dimethylaminopropyl)carbodiimide.HCl (54 mg, 0.25 mmol). The mixture was stirred overnight. Aqueous workup, as above, followed by recrystallization from ethyl acetate/hexanes provided 75 mg of compound 10b. The protecting groups were removed with 30% HBr/acetic acid (2 mL) giving compound 61b (72 mg). An analytical sample was prepared by recrystallization from methanol/ether.

Example 4

Boc-glutamyl(gamma-XAC)-alpha-benzyl ester, compound 14. XAC (compound 1a, 0.80 g), t-butyloxycarbonyl-L-glutamic acid alpha benzyl ester (Sigma Chem. Co., St. Louis, Mo., 1.5 g), and 1-hydroxybenzotriazole (0.20 g) were added to dimethylformmamide (30 ml). The suspension was treated with EDAC, ethyl-dimethylaminopropyl carbodiimide hydrochloride (1.0 g) and stirred for 2 hours. Water (60 ml) was added, and the precipitate was collected. The yield was 1.25 g (89%). The white solid was recrystallized from ethyl acetate/hexanes. The 300 MHz NMR spectrum was consistent with the assigned structure.

Example 5

Glutamic acid (gamma-XAC) alpha benzyl ester trifluoroacetate, compound 15. Compound 14 (1.25 g) was treated with trifluoroacetic acid for 10 minutes to remove the urethane protecting group. After evaporation, the residue was treated with dry ether, decanted, and dried in vacuo at 50° to give the product as a pure solid (1.01 g), in 79% yield.

Example 6

N-Acetyl-glutamic acid (gamma-XAC) alpha benzyl ester, compound 16. Compound 15 (0.77 g) was suspended in dimethylformamide (DMF, 40 ml) and treated with acetic anhydride (1 ml) and pyridine (2 ml) with agitation. Upon addition of water the product precipitated as a chromatographically pure solid and was collected by filtration and dried in vacuo. The yield was 0.40 g (57%). Analysis (C35H43N708): calc. 60.95% C, 6.28% H, 14.21% N; found 60.73% C, 6.32% H, 14.12% N.

Example 7

N-Acetyl-glutamic acid (gamma XAC), compound 17. Compound 16 (0.208 g) was suspended in 15 ml of DMF (warm). Palladium on charcoal (10%, 0.1 g) was added and the mixture was hydrogenated for 4 hours with 20 psi hydrogen gas. The reaction was judged to be complete by TLC. The catalyst was separated by centrifugation. The supernatant was treated with dry ether, and the product precipitated slowly (seeding helpful). The yield was 0.16 g (88.5%). Analysis (C28H37N708.H20): calc. 54.45% C, 6.36% H, 15.87% N; found 54.34% C, 6.30% H, 15.86% N.

Example 8

Myristoyl-XAC, compound 33. XAC (191 mg, 0.45 m mol), myristic acid (123 mg, 0.54 mol) and 1-hydroxybenzotriazole (60 mg, 1 eq) were suspended in 20 ml of dimethylformamide. EDAC (0.18 g, 2 eq) was added and the mixture was stirred for 24 hours. Saturated sodium bicarbonate solution (40 ml) was added, the solids were collected by filtration, washed (H2O), and dried in vacuo at 50°. The product (0.28 g, 98% yield) was homogenous by thin layer chromatography (Rf=0.75, silica, CHCL3:MeOH:HOAc, 85:10:5). Analysis (C35H54N605.3/2H2O) calc. 63.13% C, 8.63% H, 12.62% N; found 63.19% C, 8.47% H, 12.30% N.

Example 9

1,3-Dimyristin-2-XCC, compound 31. 1,3-Dimyristin (39.5 mg, 77 umol) and XCC (compound 30, 30 mg, 77 umol) were added to 3 ml dimethylformanide containing 20% ethanol-free chloroform. Excess EDAC (50 mg) and 4-dimethylaminopyridine (20 mg) were added, and the mixture was stirred for 24 hours. Additional chloroform (3 ml) was added and the mixture was extracted three times with phosphate buffer (pH 7). The organic layer was evaporated and the residue was recrystallized from chloroform/methanol and washed with water. The crude yield was 42 mg (49%). A homogeneous sample was obtained by preparative thin layer chromatography (silica, CHC13:MeOH:HOAc, 85:10:5).

Example 10

XCC-N-hydroxysulfosuccinimide ester. XCC was preactivated as the sulfo-N-hydroxysuccinimide ester by the following procedure: A mixture of XCC (42 mg, 0.11 mmol) and hydroxysulfosuccinimide (Pierce Chemical Co., Rockford, Ill.) in 2 ml of dimethylformamide was treated with EDAC (22 mg, 0.11 mmol). After stirring for one hour, most of the reactants had gone into solution, and TLC indicated that the reaction was nearly complete. This active ester readily acylated amines on small molecules or on biopolymers.

Example 11

XCC-phosphatidylethanolamine, compound 32. A quantity of the above solution calculated to contain 45 umol of activated xanthine intermediate was added to a solution of dioleoyl-phosphatidylethanolamine (Avanti Polar Lipids, Inc., Birmingham, Ala., 22 mg, 30 umol) in 1 ml of chloroform. The reaction was stirred for one day, and the product (13.6 mg, 27% yield) was purified by passage of the reaction mixture (volume reduced by evaporation) over a column of Sephadex LH-20, eluting with 10% chloroform in methanol.

Example 12

Hydroxy congener (8-[2-hydroxyethyl[amino[[carbonyl -[methyl[oxyphenyl]]]]]-1,3-diproprylxanthine), XHC, compound 39. XCC ethyl ester (8-[4-[(carboxymethyl)oxy]phenyl]-1,3-dipropylxanthine ethyl ester, 63 mg, 0.15 mmol) was dissolved in 3 ml of ethanolamine and warmed (50°) for one hour. The volume was reduced in vacuo. The product crystallized slowly upon addition of methanol/ether/petroleum ether, to give the pure product (59 mg, 90% yield). The NMR and mass spectra (CI) were consistent with the assigned structure.

Example 13

Elaidic ester of hydroxy congener, compound 42. The hydroxy congener (above, 74 mg, 0.17 mmol) and elaidic anhydride (215 mg, 0.39 mmol, Sigma Chemical Co., St. Louis, Mo.) were added to an equivolume mixture of methylene chloride and dimethylformamide (10 ml) and treated with 4-dimethylaminopyridine (30 mg). After stirring for one day the reaction was judged by thin layer chromatography to have reached approximately 70% completion. Water was added, and the organic phase was washed successively with sodium bicarbonate and sodium bisulfate. The organic layer was reduced in volume, and the product was purified by preparative thin layer chromatography (CHC13:MeOH:HOAc, 90:5:5). A fast running band was isolated and eluted with methanol:chloroform (1:1). The solvent was evaporated, and the residue was collected and washed with a small amount of cold methanol. The NMR spectrum of the product (60 mg, 50% yield) was consistent with the assigned structure. The IR spectra showed the expected ester carbonyl resonance band.

Example 14

Stearoyl-ADAC, compound 41. ADAC (38 mg, 66 umol) was suspended in dimethylformamide (5 ml) and treated with a solution of stearic anhydride (90 mg, 163 umol, Sigma Chemmical Co., St. Louis, Mo.) in 2 ml of methylene chloride. After the mixture was warmed to 50° for 10 minutes, thin layer chromatography showed the reaction to be complete. The product (Rf 0.43, CHC13:MeOH:HOAc, 85:10:5, silica) was isolated as a precipitate upon addition of methylene chloride and dry ether. The yield was 30 mg (54% yield).

Example 15

N-FMOC-Iminodiacetic acid. Iminodiacetic acid (2.19 g, 16.5 mmol, Sigma Chemical Co., St. Louis, Mo.) was dissolved in a mixture of 1 M sodium bicarbonate (40 ml) and acetone (30 ml). 9-Fluorenemethyl chloroformate (2.0 g, 7.7 mmol) was dissolved in acetone (10 ml) and added to the above solution. After 6 hours reaction, the mixture was treated with brine, acidified with 1N HCl, and extracted with ethyl acetate. The yield was 2.38 g (87%), mp 213°–215.5° C. The mass spectrum (CI-NH3) showed a peak at 373 corresponding to m+1+NH3. Analysis (C19H17N06): calc. 64.22% C, 4.82% H, 3.94% N; found 64.15% C, 4.83% H, 3.909% N.

Example 16

4-FMOC-morpholine-2,6-dione. N-FMOC-Iminodiacetic acid (0.40 g, 1.13 mmol) was suspended in 30 ml ethyl acetate and treated with 1 ml of trifluoracetic anhydride. After stirring for one hour, most of the solvent was evaporated. Petroleum ether was added, followed by evaporation, resulting in a solid residue was dried in vacuo at room temperature. The yield was 0.37 g (97%) mp 180°–185° C.

Example 17

8-[N -Carboxymethyl-N -(9-fluorenylmethyloxycarbonyl) -[[[[[[[[amino]methyl]carbonyl]amino]ethyl]amino]carbonyl]methyl]-oxy]phenyl]-1,3-dipropylxanthine, compound 44. N -N -4-FMOC-morpholine-2,6-dione (33 mg, 0.10 mmol) was dissolved in 4 ml of an equivolume mixture of dimethylformamide and ethyl acetate. XAC (compound 1, 36 mg, 83 umol) was added and the mixture was warmed (50°) for one hour. The volume was reduced by one half by evaporation, and sodium bisulfate (1 M) was added. The precipitate was collected and dried in vacuo to give 50 mg (78% yield) of product. This could be recrystallized from ethyl acetate/petroleum ether. The NMR spectrum was consistent with the assigned structure. Analysis (C40H43N709.3/2H2O): calc. 60.60% C, 5.85% H, 12.37% N; found 60.58% C, 5.79% H, 12.27% N.

TABLE 1

Representative Prodrugs

| Prodrug (and Cleavage Sites) | Type of Cleavage | Liberated Product | $K_i$(nM) at $A_1$ Before Cleavage | $K_i$(nM) at $A_1$ After Cleavage |
|---|---|---|---|---|
| 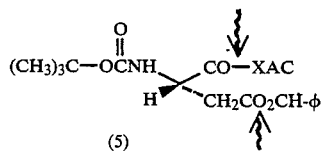 (5) | esterolysis, then proteolysis | 1a | 150 | 1.2 |
| 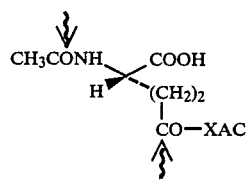 (17) | proteolysis, γ-Glutamyl substitution | 1a | 240 | 1.2 |
| 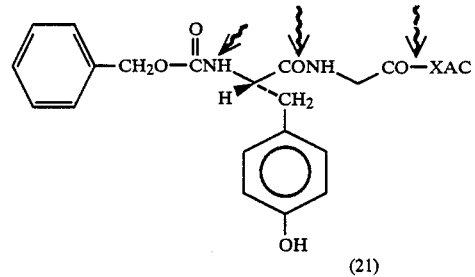 (21) | proteolysis, hydrolysis of urethane | 1a<br>22<br>H—Gly—XAC | 4<br>4<br>4 | 1.2<br>5.3<br>2.1 |

TABLE 1-continued
Representative Prodrugs
| Prodrug (and Cleavage Sites) | Type of Cleavage | Liberated Product | Ki(nM) at A₁ Before Cleavage | Ki(nM) at A₁ After Cleavage |
|---|---|---|---|---|
| 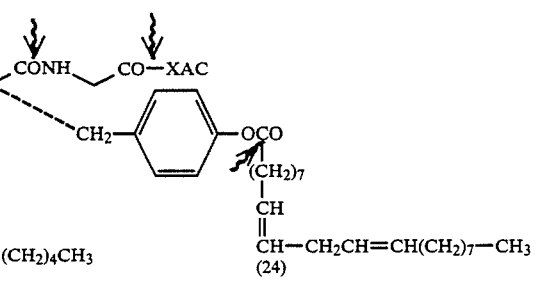 (24) | esterolysis, proteolysis | 1a 22 H—Gly—XAC | 20 20 20 | 1.2 5.3 2.1 |
| 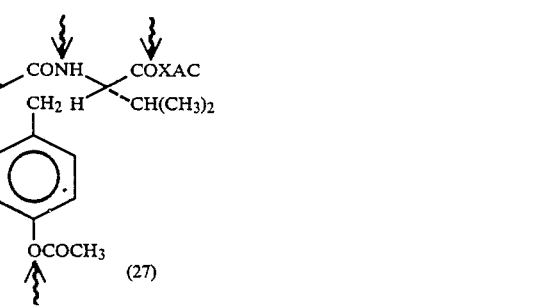 (27) | esterolysis proteolysis | 1a 26 H—Val—XAC | 5.0 5.0 5.0 | 1.2 3.0 3.0 |
| 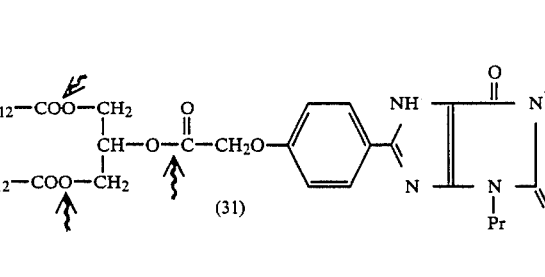 (31) | esterolysis | 30 | 104 | 58 |
| 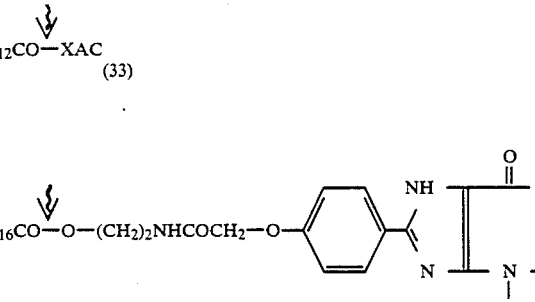 (33) | hydrolysis | 1a | 49 | 1.2 |
| 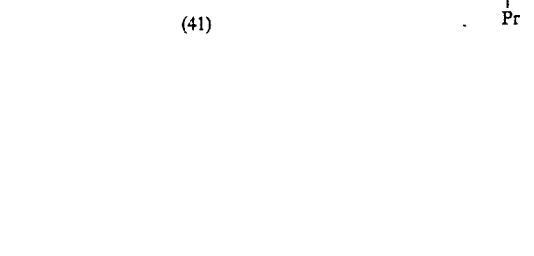 (41) | esterolysis | 39 | 208 | 12 |

TABLE 1-continued

Representative Prodrugs

| Prodrug (and Cleavage Sites) | Type of Cleavage | Liberated Product | Ki(nM) at A₁ Before Cleavage | Ki(nM) at A₁ After Cleavage |
|---|---|---|---|---|
| 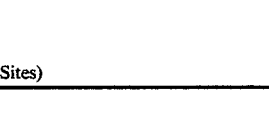 | oxidation, then hydrolysis | 43 1a | — 10 | 10 1.2 |

TABLE 2

Adenosine receptor ligands and biologically active intermediates.

| Derivative | mp | synth.* | % yld | Ki (A1(nM)) |
|---|---|---|---|---|
| 1a. XAC | 218–220 | A | | 1.2 ± 0.5 |
| 1b. ADAC | 221–223 | A | | 0.85 |
| 2. N—Cbz—XAC | 150–160 | B(1) | 60 | 8 |
| 3. N—Cbz—(N7-benzyl)XAC | | C(2) | 43 | 95 |
| 4. (N7-benzyl)XAC | | D(3) | 90 | 250 |
| 5. Boc—Asp(O—Bzl)—XAC | 199–201 | B(1) | 96 | 150 |
| 6. Boc—Asp—XAC | | E(5) | 100 | 30 |
| 7. Ac—Leu—XAC | 273–275 | B(1) | 51 | 20 |
| 8. Ac—Tyr—XAC | | B(1) | | n.d. |
| 9. Boc—D—(p-NO₂)Phe—XAC | 197–199 | B(1) | 66 | 89 |
| 10. Boc—D—(p-NH₂)Phe—XAC | 201–205d | E(9) | 94 | 32 |
| 11. TFA.H—D—(p-NO₂)Phe—XAC | 165–169 | D(10) | 90 | 4.3 |
| 12. TFA.H—D—(p-NH₂)Phe—XAC | 233–237 | E(11) | 54 | 2.3 |
| 13. TFA.H—D—(p-NH₂-m-I)Phe—XAC | | F(12) | 50 | 4 |
| 14. Boc—Glu(XAC)—OBzl | 200–205 | B(1) | 89 | 18 |
| 15. TFA.H—Glu(XAC)—OBzl | 128–132 | D(14) | 79 | 1.8 |
| 16. Ac—Glu(XAC)— | 238–243 | B(15) | 57 | 9.8 |
| 17. Ac—Glu(XAC)—OH | 222–225 | E(16) | 88 | 240 |
| 18. H—Glu(XAC)—OH | 196–198 | E(15) | 68 | 17 |
| 19. Cbz—Gly—Gly—XAC | 220–225 | B(1) | 96 | 3.1 |
| 20. HBr.H—Gly—Gly—XAC | 165–170d | D(19) | 66 | 3.6 |
| 21. Cbz—Tyr—Gly—XAC | 195–198 | B(1) | 75 | 4 |
| 22. HBr.H—Tyr—Gly—XAC | d. begin 170 | D(21) | 87 | 5.3 |
| 23. Ac—Tyr—(O—Ac)—Gly—XAC | 220d | B(22) | 80 | 3.9 |
| 24. Linoleyl-Tyr(O-linoleyl)-Gly—XAC | 175–179 | B(22) | 40 | 20 |
| 25. Cbz—Tyr—Val—XAC | 263–268 | B(1) | 75 | 3.7 |
| 26. HBr.H—Tyr—Val—XAC | 218d | D(25) | 94 | 3.0 |
| 27. Ac—Tyr(O—Ac)—Val—XAC | 277–280 | B(26) | 78 | 5.0 |
| 28. Cbz—Gly—Gly—Gly—XAC | 235–239d | B(1) | 47 | 10 |
| 29. HBr.H—Gly—Gly—Gly—XAC | 250–255 | D(28) | 90 | 10 |
| 30. XCC | 283–285 | | | 58 ± 3 |
| 31. 1,3-dimyristin-(2-XCC) | amorph. solid | B(30) | 49 | 104.4 ± 7.7 |
| 32. (N—XCC)—PE | amorph. solid | B(30) | 27 | 24 ± 1 |
| 33. N-myristoyl-XAC | 228–230 | B(1) | 98 | 98 ± 16 |
| 34. N-linoleyl-XAC | 218–224 | B(1) | 30 | 35 |
| 35. Ac—Glu(ADAC)—OH | | Scheme 2 | | >10 |
| 36. N-stearoyl-ADAC | 254–256 | B(35) | 54 | 1.0 |
| 37. N-elaidoyl-ADAC | 252–254 | B(35) | 100 | <0.3 |
| 38. N-linoleyl-ADAC | 228–235 | B(35) | 87 | 0.5 |
| 39. XHC | 272–275d | A | 91 | 13 |
| 40. O—Ac—XHC | 220–222 | B(39) | 80 | 12 |
| 41. O-stearoyl-XHC | dec. beg. 150 | B(39) | 50 | 208 |
| 42. O-elaidoyl-XHC | 90–110 | B(39) | 70 | 85 |

TABLE 2-continued
Adenosine receptor ligands and biologically active intermediates.

| Derivative | mp | synth.* | % yld | Ki (A1(nM)) |
|---|---|---|---|---|
| 43. 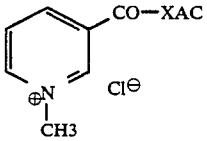 | | B(1) | | 40 |
| 44. HO₂CCH₂—N(FMOC)CH₂CO—XAC | | B(1) | 78 | 170 |
| 45. HO₂CCH₂—NHCH₂CO—XAC | | (44) | 95 | n.d. | abbreviations:
XHC, xanthine hydroxy congener, compound 39

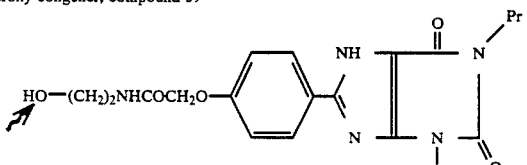

acylation site

XAC, xanthine amine congener, compound 1a

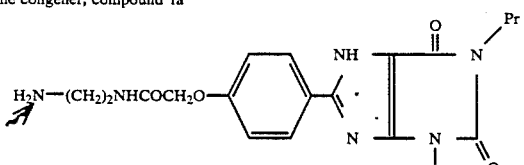

acylation site

XCC, xanthine carboxylic acid congener, compound 30

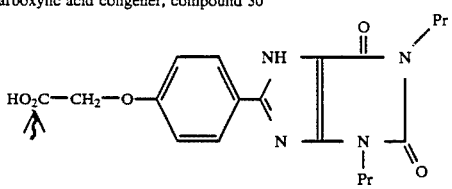

acylating group

ADAC, adenosine amine congener, compound 1b

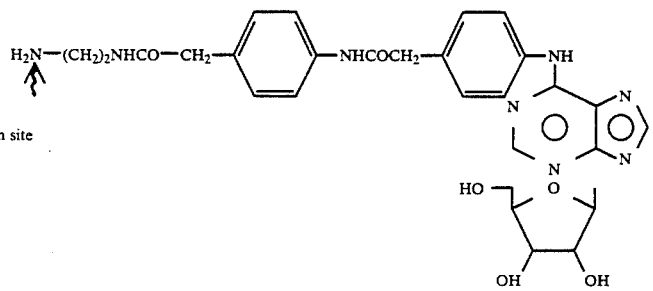

acylation site

PE, dioleylphosphatidylethanolamine.
*key to reaction types (starting material in parentheses)
A aminolysis (eg. neat ethanolamine)
B acylation (eg. carboxylic anhydride or carboxylic acid plus carbodiimide, dimethylaminopyridine for ester formation)
C alkylation (eg. benzyl bromide)
D anhydrous acid cleavage (eg. trifluoracetic acid or 30% HBr/acetic acid)
E catalytic hydrogenation (eg. over Pt or Pd catalyst)
F iodination (eg. iodide and chloramine-T)
Chiral amino acids are of the L-configuration unless noted.

TABLE 3
Diuretic Effects of XAC and the Ac-gamma-Glu Prodrug After Administration of N⁶-cyclo-hexyladenosine in Rats

| Xanthine | Dose | % of normal glomerular filtration rate | n = |
|---|---|---|---|
| XAC | low | 39.6 (before) 58.2 (after) | 3 |
| XAC | 10 × low | 37.4 (before) 67.3 (after) | 8 |
| Cmpd 17 | 10 × low | 48 (before) 84.8 (after) | 7 |

TABLE 4
Selective Kidney Effects of Prodrug in Rats

| | b.p. (mmHg) | Sodium excretion (uEq/min/kg) | n = |
|---|---|---|---|
| Control | 137.1 + 1.6 | 6.21 + 0.48 | 7 |
| CHA[1] | 113 + 2 | 0.86 + 0.04 | 5 |
| CHA + XAC[2](1a) | 130.6 + 1.6 | 2.37 + 0.43 | 4 |
| CHA + Compd. 17[2] | 103.5 + 3.5 | 2.12 + 0.36 | 5 |

[1]CHA = N⁶-cyclohexyladenosine - administered as a constant infusion of 10 nanmoles/min./kg. Total dose administered over 45 min. was approximately 40 ug/kg (= relatively high dose).
[2]Xanthine antagonists were administered in a bolus injection of 0.2 umoles/kg followed by an infusion of 2 nanamoles per kg/min.

TABLE 5

Synthesis and characterization[e] of new xanthine derivatives (compound suffixes a, b, and c refer to R = Me, Et, and Pr, respectively).

| Cmpd. | % Yield | mp (°C.) | formula | analysis |
|---|---|---|---|---|
| 52b | 67[a] | >310 | $C_{17}H_{18}N_4O_5 \cdot H_2O$ | C,H,N |
| 53a | 61 | 294–296 | $C_{17}H_{18}N_4O_5 \cdot \frac{1}{4}H_2O$ | C,H,N |
| 53b | 86 | 267–269 | $C_{19}H_{22}N_4O_5$ | C,H,N |
| 54b | 71 | 275–277 | $C_{20}H_{24}N_4O_5 \cdot \frac{1}{2}DMF$ | C,H,N |
| 55b | 88 | 300–302 | $C_{19}H_{23}N_5O_4 \cdot \frac{1}{2}H_2O$ | C,H,N |
| 56a | 99 | 255–258 | $C_{17}H_{20}N_6O_4 \cdot \frac{1}{4}H_2O$ | C,H,N |
| 56b | 92 | 233–235 | $C_{19}H_{24}N_6O_4 \cdot H_2O \cdot DMF$ | C;H,N[b] |
| 57b | 58 | >310 | $C_{24}H_{25}N_5O_4 \cdot 4/5H_2O$ | C,H,N |
| 58a | 60 | >310 | $C_{24}H_{23}N_5O_6$ | H,N;C[c] |
| 58b | 92 | 310–313 | $C_{26}H_{27}N_5O_6 \cdot \frac{1}{2}H_2O$ | C,H,N |
| 59a | 94 | decomp 280 | $C_{25}H_{27}N_7O_5$ | H,N;C[d] |
| 59b | 77 | 273–278d | $C_{27}H_{31}N_7O_5 \cdot \frac{3}{4}H_2O$ | C,H,N |
| 60b | 79 | 215–219 | $C_{38}H_{50}N_8O_9 \cdot \frac{1}{2}H_2O$ | C,H,N |
| 60c | 95 | 207–211 | $C_{40}H_{54}N_8O_9$ | C,H,N |
| 61b | 100 | 270–275 | $C_{25}H_{36}N_8O_5 \cdot 2HBr \cdot 2H_2O$ | C,H,N |
| 61c | 83 | d begin 190 | $C_{27}H_{40}N_8O_5 \cdot 3HBr$ | C,H,N |

[a] Yield calculated from 6-amino-1,3-diethyl-5-nitrosouracil, which was treated with $Na_2S_2O_4$ and then condensed with 4-formyloxyacetic acid, and the benzylidiene adduct was oxidized with $NaIO_4$.
[b] H calc 6.77, found 6.25; N calc 19.95, found 18.97.
[c] C calc 60.37, found 52.82.
[d] C calc 59.40, found 51.49.
[e] Proton NMR resonances (300 MHz) in ppm from TMS for selected compounds in $(CD_3)_2SO$:

56b δ 8.15 (t, 1H, amide NH), 8.05 and 7.05 (each d, J = 8.7 Hz, 2H, Ar), 4.54 (s, 2H, $CH_2O$), 4.08 and 3.94 (each q, 2H, Et methylene), 3.21 (m, 2H, $\underline{CH_2}NHCO$), 2.68 (t, J = 6.2 Hz, 2H, $\underline{CH_2}NH_2$), 1.26 and 1.13 (each t, 2H J = 6.8 Hz, $CH_3$).
58a δ 8.10 (d, 2H, Ar, meta to O), 7.58 (d, 2H, Ar, ortho to NH), 7.23 (d, 2H, Ar, ortho to $CH_2$), 7.13 (d, 2H, Ar, ortho to O), 4.79 (s, 2H, $CH_2O$), 3.63 (s, 2H, $CH_2Ar$), 3.61 (s, 3H, $OCH_3$), 3.49 and 3.27 (each s, 3H, $NCH_3$).
59a δ 8.06 (d, 2H, Ar, meta to O), 8.02 (1H; amide NH), 7.56 (d, 2H, Ar, ortho to NH), 7.21 (d, 2H, Ar, ortho to $CH_2$), 7.13 (d, 2H, Ar, ortho to O), 4.75 (s, 2H, $CH_2O$), 3.48 and 3.24 (each s, 3H, $NCH_3$), 3.36 (s, 2H, $CH_2Ar$), 3.07 (m, 2H, $\underline{CH_2}NHCO$), 2.60 (t, J = 6.7 Hz, 2H, $\underline{CH_2}NH_2$).

TABLE 6

Potencies of xanthine derivatives at $A_2$ and $A_1$ adenosine receptors.

| Cmpd. | R =[a] | $A_2$ receptor[b] $K_B$ (nM) | $A_1$ receptor[c] $K_i$ (nM) |
|---|---|---|---|
| 51a | Me | 1,900 | 70 |
| 51b | Et | 210 | 65 |
| 51c | Pr | 2,100 | 13 |
| 52c | Pr | 2,400 (1,500–3,900) | 50 |
| 53b | Et | 170 (75–370) | 140 |
| 53c | Pr | 135 (106–173) | 13 |
| 54b | Et | 73 (54–98) | 90 |
| 55b | Et | 48 (36–65) | 57 |
| 56a | Me | 40 (30–54) | 13 |
| 56b | Et | 21 (18–23) | 12 |
| 56c (=1a) | Pr | 25 (21–30) | 1.2 (XAC) |
| 57a | Me | 430 (260–720) | 27 |
| 57b | Et | 100 (60–170) | 9.3 |
| 58b | Et | 210 (190–230) | 58 |
| 59a | Me | 63 (57–68) | 42 |
| 59b | Et | 28 (15–51) | 25 |
| 60b | Et | 230 (100–540) | 180 |
| 61b | Et | 23 (17–30) | 9.4 |
| 61c | Pr | 37 (35–40) | 0.87 |

[a] Substituent at the 1,3-positions.
[b] Antagonism of NECA-induced stimulation of adenylate cyclase activity in human platelet membranes. Values are means with 95% confidence limits from 3 separate experiments.
[c] Inhibition of [³H]PIA binding to rat cerebral cortex membranes. Values are means from two separate experiments.

We claim:

1. A compound of the formula:

$$Z^N - B_n - A_m - CO - CH_2 - D$$
$$\quad\quad\, |\quad\, |$$
$$\quad\quad Z_B\ Z_A$$

wherein:

D is a moiety of the formula:

Formula Q (structure shown with $R_7$, $R_1$, $R_3$, Y substituents on fused ring system)

or of the formula:

Formula R (structure shown with NH linkage, heterocyclic ring, and ribose with HO, OH, OH)

$R_1$ and $R_3 = C_1$-$C_6$ alkyl;
$R_7 =$ hydrogen or benzyl;
Y = H, OH, OMe, Halo, or amine;
A and B = cleavable linking groups selected from the group consisting of an amino group, an amino acid, a peptide containing up to three amino acids, an ethylenediamino group, a phospholipid, and a fatty acid;
n and m = 0, 1, with the proviso that at least one of n or m is 1;
$Z^N =$ H, an amino blocking group, or a group of the formula:

Formula K $$R_9 - NH - CH - COOR_{15}$$
$$\quad\quad\quad\quad\, |$$
$$\quad\quad\quad\, (CH_2)_2$$
$$\quad\quad\quad\quad\, |$$
$$\quad\quad\quad\, CO-$$

$R_{10} = C_1$-$C_6$ alkyl
$R_{15} =$ H, alkyl, phenyl, or benzyl;
$Z_A$, $Z_B =$ H or amino acid side chain blocking groups;
and B-A, $Z^N$-B, $Z_B$-B, $Z_A$-A, and A-CO = groups cleavable in vivo which have amide, ester, or urethane bonds.

2. Compounds of the formula:

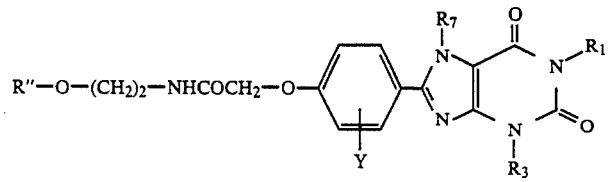

wherein
$R_1$, $R_3 = C_1-C_6$;
$R_7 =$ hydrogen or benzyl;
$Y = H$, OH, OMe, halo or amine; and
$R'' = H$ or fatty acid.

3. A compound of claim 1 wherein $Z^N$ is formula K.
4. A compound of claim 3 wherein D is formula Q.
5. A compound of claim 3 wherein D is formula R.
6. A compound of claim 3 wherein $R_{15}$ is alkyl, phenyl, or benzyl.
7. A compound of claim 1 wherein D is formula R.
8. A compound of claim 1 wherein D is formula Q.
9. A compound of the formula:

L-G-A-CO-CH$_2$-E wherein:
L = phospholipid or fatty acid;
G = amide, ester, or urethane linkage;
A is a spacer, selected from the group consisting of —NH—(CH$_2$)$_2$—NH—,

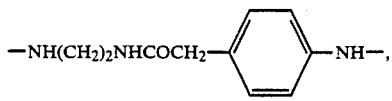

a peptide containing up to three amino acids, and an amino acid; and
E is the formula:

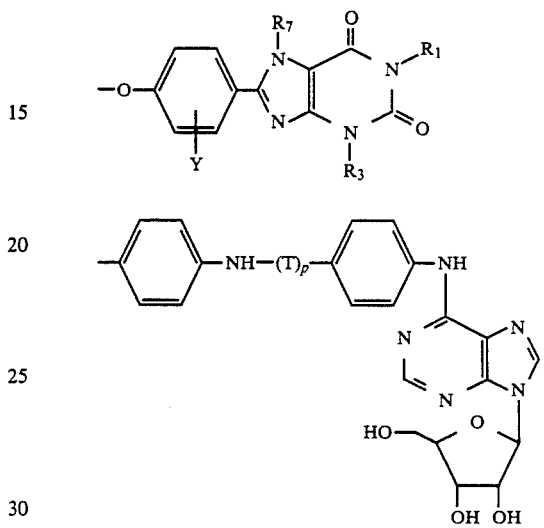

wherein,
$R_1$ and $R_3$ are $C_1-C_6$ alkyl;
$R_7 =$ hydrogen or benzyl;
$Y =$ OH, OMe, Halo, or amine;
$T = COCH_2$; and p is 0 or 1;

10. A compound of claim 9 wherein A is —NH(CH$_2$)$_2$NH— or

—NH(CH$_2$)$_2$NHCOCH$_2$—⟨phenyl⟩—NH—.

11. A pharmaceutical composition which comprises a compound of claim 1 in a pharmaceutically acceptable carrier.

12. A pharmaceutical composition which comprises a compound of claim 3 in a pharmaceutically acceptable carrier.

13. A pharmaceutical composition which comprises a compound of claim 9 in a pharmaceutically acceptable carrier.

* * * * *